(12) United States Patent
Bardy

(10) Patent No.: US 6,436,068 B1
(45) Date of Patent: Aug. 20, 2002

(54) INSTRUMENT FOR IMPLANTING SENSORS AND SOLID MATERIALS IN A SUBCUTANEOUS LOCATION AND METHOD THEREOF

(76) Inventor: Gust H. Bardy, 2518 Constance Dr. W., Seattle, WA (US) 98199-3017

( * ) Notice: Subject to any disclaimer, the term of this patent is extended or adjusted under 35 U.S.C. 154(b) by 138 days.

(21) Appl. No.: 09/644,666

(22) Filed: Aug. 24, 2000

(51) Int. Cl.[7] .............................................. A61M 31/00
(52) U.S. Cl. ............................ 604/57; 604/59; 604/60
(58) Field of Search .............................. 604/57, 58, 59, 604/60, 61, 62, 63, 65

(56) References Cited

U.S. PATENT DOCUMENTS

| | | | | |
|---|---|---|---|---|
| 4,447,223 A | * | 5/1984 | Kaye et al. ................... | 604/61 |
| 4,531,938 A | * | 7/1985 | Kaye et al. ................... | 604/62 |
| 4,769,011 A | * | 9/1988 | Swaniger .................... | 604/218 |
| 4,832,687 A | | 5/1989 | Smith, III | |
| 4,900,304 A | * | 2/1990 | Fujioka et al. ................ | 604/60 |
| 4,909,250 A | | 3/1990 | Smith | |
| 4,915,686 A | * | 4/1990 | Frederick ..................... | 604/60 |
| 4,936,827 A | * | 6/1990 | Grimm et al. ................ | 604/60 |
| 4,941,874 A | * | 7/1990 | Sandow et al. ............... | 604/60 |
| 4,950,234 A | * | 8/1990 | Fujioka et al. ................ | 604/60 |
| 5,250,026 A | * | 10/1993 | Ehrlich et al. ................ | 604/60 |
| 5,273,532 A | * | 12/1993 | Niezink et al. ............... | 604/62 |
| 5,279,554 A | * | 1/1994 | Turley ........................ | 604/60 |
| 5,279,555 A | * | 1/1994 | Lifshey ....................... | 604/60 |
| 5,284,479 A | * | 2/1994 | de Jong ...................... | 604/60 |
| 5,300,106 A | | 4/1994 | Dahl et al. | |
| 5,304,119 A | | 4/1994 | Balaban et al. | |
| 5,358,474 A | * | 10/1994 | Kaldany ...................... | 604/57 |
| 5,405,324 A | * | 4/1995 | Wiegerinck .................. | 604/60 |
| 5,484,403 A | * | 1/1996 | Yoakum et al. ............... | 604/59 |
| 5,501,664 A | * | 3/1996 | Kaldany ...................... | 604/57 |
| 5,507,807 A | * | 4/1996 | Shippert ...................... | 623/8 |
| 5,526,772 A | | 6/1996 | Curkendall | |
| 5,558,637 A | * | 9/1996 | Allonen et al. ............... | 604/60 |
| 5,562,613 A | * | 10/1996 | Kaldany ...................... | 604/57 |
| 5,772,671 A | * | 6/1998 | Harmon ..................... | 606/117 |
| 5,810,769 A | * | 9/1998 | Schlegel et al. .............. | 604/59 |
| 5,827,293 A | * | 10/1998 | Elliot ......................... | 606/107 |
| 5,908,404 A | * | 6/1999 | Elliot ......................... | 604/51 |
| 5,944,732 A | | 8/1999 | Raulerson et al. | |
| 5,984,890 A | * | 11/1999 | Gast et al. .................... | 604/60 |
| 6,190,350 B1 | * | 2/2001 | Davis et al. .................. | 604/61 |
| 6,245,052 B1 | * | 6/2001 | Orth et al. ................... | 604/506 |

FOREIGN PATENT DOCUMENTS

| WO | PCT/US99/08353 | 4/1999 |
|---|---|---|
| WO | PCT/GB99/02389 | 7/1999 |
| WO | PCT/GB99/02393 | 7/1999 |

\* cited by examiner

*Primary Examiner*—Denise L. Esquivel
*Assistant Examiner*—Marc Norman
(74) *Attorney, Agent, or Firm*—Patrick J.S. Inouye

(57) ABSTRACT

An implantation instrument for implanting a sensor or substantially solid material, including solid medication or drugs, in a subcutaneous location and method thereof are described. An incising shaft includes a beveled tip with a cutting edge along a distal end thereof. A syringe body is affixed to a proximal end of the incising shaft. The syringe body and the incising shaft each define a substantially non-circular hollow bore extending continuously along a shared longitudinal axis. The incising shaft bore does not exceed the syringe body bore in girth. Both the incising shaft bore and the syringe body bore are sized to receive the solid material. A plunger is conformably shaped to the syringe body bore and has an end piece facilitating deployment of the plunger assembly. The plunger slidably fits within the syringe body bore and advances the solid material through the syringe body bore and the incising shaft bore into the subcutaneous location.

12 Claims, 5 Drawing Sheets

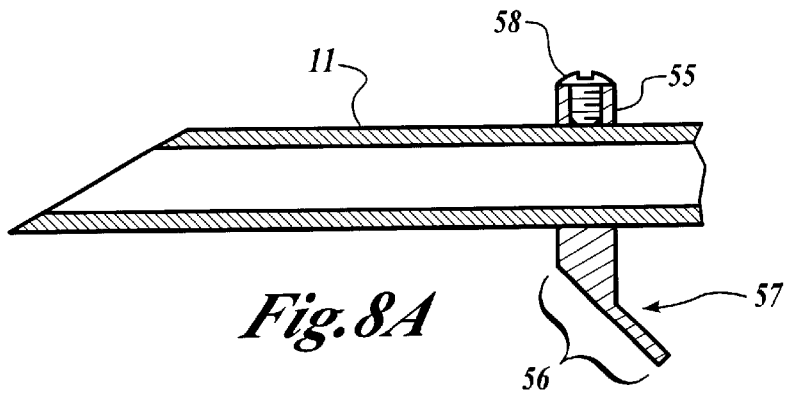
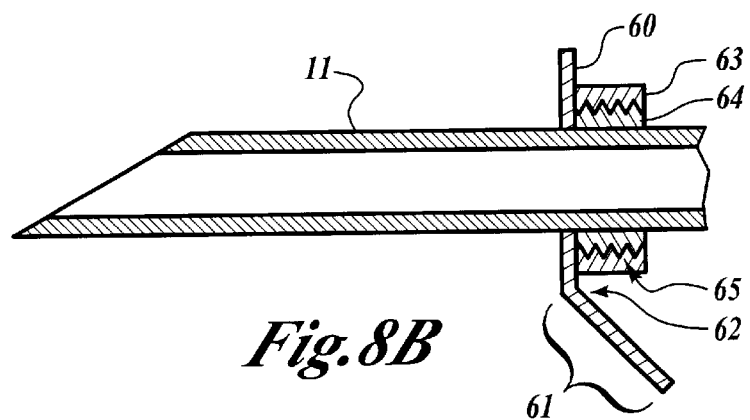
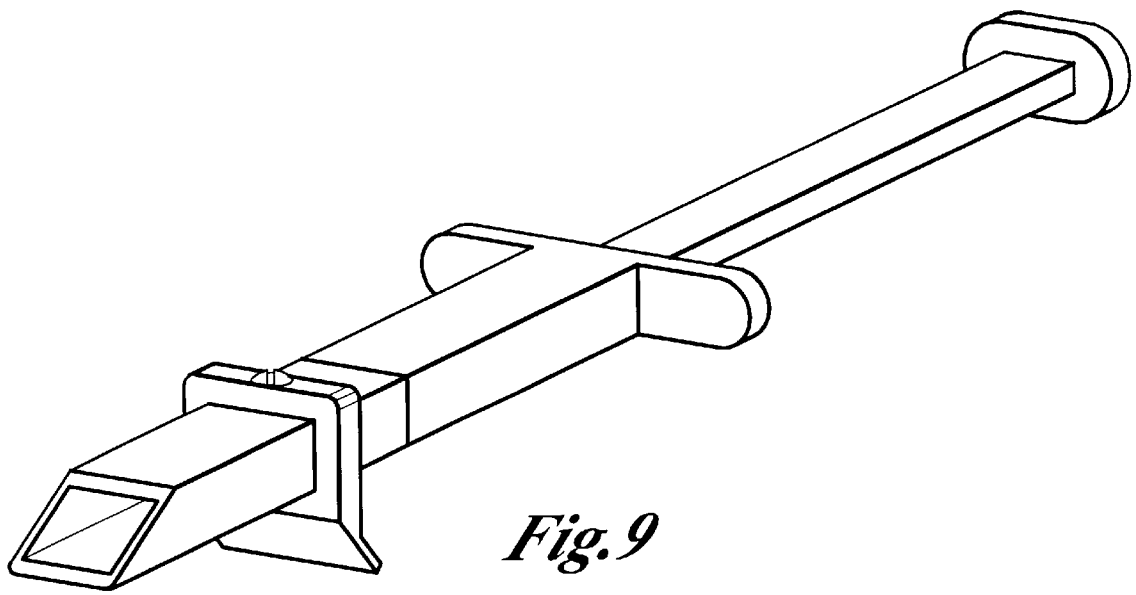

INSTRUMENT FOR IMPLANTING SENSORS AND SOLID MATERIALS IN A SUBCUTANEOUS LOCATION AND METHOD THEREOF

FIELD OF THE INVENTION

The present invention relates in general to subcutaneous implantation instruments and methods and, in particular, to an instrument for implanting sensors and solid materials in a subcutaneous location and method thereof.

BACKGROUND OF THE INVENTION

A major part of health care assessment involves the review and analysis of physiological measurements collected and recorded by electronic data sensors. In addition to vital signs, physiological measures can include detailed measurements of organ functions, body fluid chemistry and rates, activity levels, and similar measures, both measured directly and derived.

The type and quality of physiological measures depends greatly on the type and location of the sensor employed. External sensors, such as thermometers, blood pressure cuffs, heart rate monitors, and the like, constitute the most common, and least invasive, form of sensors. However, these sensors are extremely limited in the kinds of information which they are able to collect and encumber the patient with wearing and maintaining an external sensor. On the other extreme, implantable in situ sensors provide the most accurate and continuous data stream through immediate proximity to organs and tissue of interest. However, implantable sensors are invasive and generally require surgery for implantation.

Recent advances in microchip technology have created a new generation of highly integrated, implantable sensors. For instance, PCT Application Nos. PCT/GB99/02389, to Habib et al., filed Jul. 22, 1998, pending, and PCT/GB99/02393, to Habib et al., filed Jul. 22, 1998, pending, respectively describe an implantable sensor chip and treatment regiment, the disclosures of which are incorporated herein by reference. The sensor chip is adapted to receive and rectify incoming electromagnetic signals and to transmit data relating to treatment parameters by wireless telemetry to a receiver external to a body. Similarly, the emerging Bluetooth wireless communication standard, described at http://www.bluetooth.com/developer/specification/specification.asp, proposes a low cost, small form factor solution to short range data communications, potentially suitable for use in implantable sensor technology.

Even though implantable sensor technology is trending towards smaller and more specialized microchip sensors, in humans, these sensors must still be implanted via surgical procedure. Minimally invasive implantation using large bore needles is impracticable because sensors, particularly when embodied using microchip technology, favor a prismatic shape with substantially rectangular cross sections. A large bore needle can cause a core of flesh or skin (or hide, when used in domesticated animals) to form in the pointed tip as the needle is inserted. Cylindrical needles also severely limit solid sensor sizes, shapes and dimensions to only those that can be inserted through a circular bore.

Although current surgical approaches attempt to minimize the size of incision and decree of invasion, implantation is, at best, costly, time-consuming, traumatic, requires multiple instruments and maneuvers, and potentially risky to the patient. Subcutaneous implantable sensors offer the best compromise between in situ sensors and external sensors and are potentially insertable with a simple injection. These sensors are typically implanted below the dermis in the layer of subcutaneous fat. The subcutaneous implantation of solid materials has been described in the prior art as follows. An insertion and tunneling tool for a subcutaneous wire patch electrode is described in U.S. Pat. No. 5,300,106, to Dahl et al., issued Apr. 5, 1994. The tunneling tool includes a stylet and a peel-away sheath. The tunneling tool is inserted into an incision and the stylet is withdrawn once the tunneling tool reaches a desired position. An electrode segment is inserted into the subcutaneous tunnel and the peel-away sheath is removed. Although providing a tool for subcutaneous implantation, the Dahl device requires an incision into the subcutaneous fat layer and forms an implantation site larger than the minimum sized required by the electrode segment. Further more, the cylindrical bore precludes the injection of non-conforming solid sensors or materials.

An implant system for animal identification that includes a device for implanting an identification pellet in a fat layer beneath the hide or skin of an animal is described in U.S. Pat. No. 4,909,250, to Smith, issued Mar. 20, 1990. The device includes a curved needle-like tube that terminates at a tapered, sharpened point. An elongated, flexible plunger is slidably received within the needle-like tube. The pointed tip is inserted through the hide or skin and the plunger is actuated to drive the identification pellet from the tip into the fat layer. However, the Smith device uses an oversized open bore which can cause coring of the hide or flesh.

A trocar for inserting implants is described in PCT Application No. PCT/US99/08353, to Clarke et al., filed Oct. 29, 1999, pending. An implant retention trocar includes a cannula for puncturing the skin of an animal and an obturator for delivering the implant. A spring element received within the cannula prevents an implant from falling out during the implant process. The cannula has a distal tip design which causes a minimum of trauma and tearing of tissue during implant insertion. However, the distal tip design is specifically directed to cannulas having a substantially circular bore and thereby limits the size and shape of implant which can be inserted through the Clarke trocar.

An instrument for injecting implants through animal hide is described in U.S. Pat. No. 5,304,119, to Balaban et al., issued Apr. 19, 1994. The instrument includes an injector having a tubular body divided into two adjacent segments with a hollow interior bore. A pair of laterally adjacent tines extend longitudinally from the first segment to the distal end of the tubular body. A plunger rod has an exterior diameter just slightly larger than the interior diameter of the tubular body. With the second segment inserted beneath the animal hide, the push rod is advanced longitudinally through the tubular body, thereby pushing the implant through the bore. As the implant and rod pass through the second segment, the tines are forced radially away from each other, thereby dilating or expanding the incision, and facilitating implant. The instrument is removed from the incision following implantation. Though avoiding the coring of animal hide or flesh, the instrument forms an implantation site larger than the minimum sized required by the implant and causes potentially damaging compaction of the implant against the laterally adjacent times during implant delivery.

Therefore, there is need for a non-surgical instrument and method for subcutaneous implantation of sensors and solid materials that preferably does not require an incision preparatory to instrument insertion.

There is a further need for a subcutaneous implantation instrument and method capable of implanting sensors and other solid materials that are not readily disposed to implantation through a substantially circular bore.

Moreover, there is a further need for a subcutaneous implantation instrument and method which is minimally invasive, preferably creating the smallest needed implantation site, and capable of implantation without exposing the implant to longitudinal stresses.

SUMMARY OF THE INVENTION

The present invention provides an implantation instrument and method of use for implanting sensors and other solid materials in a subcutaneous or other site. As used herein, "subcutaneous" refers generally to those implantation sites located within a body below the skin. The implantation instrument consists of an incising shaft attached to a syringe body. The syringe body and incising shaft both define a substantially non-circular hollow bore for accommodating the sensor or solid material. The subcutaneous site is formed by a cutting edge on the distal end of the incising shaft. The subcutaneous site can be cleared using a clearing trocar slidably received within the hollow bore. The sensor or solid material is advanced through the hollow bore and delivered into the subcutaneous site. The depth of the subcutaneous site can be limited using a penetration limiting mechanism.

An embodiment of the present invention is an implantation instrument for implanting a substantially solid material in a subcutaneous body location. An incising shaft defines a substantially non-circular hollow bore extending continuously along a longitudinal axis. The incising shaft has a beveled tip forming a cutting edge on a distal end thereof and is sized to receive a substantially solid material for implant. The solid material, which can include a sensor, is preferably protected against damage by encasement within, for example, a mannitol pellet or similar carrier. The solid material can also be encased in titanium, silicone, epoxy, or other similar, functionally inert protective material. A delivery mechanism receives the incising shaft and includes a pushing device facilitating deployment of the substantially solid material through the incising shaft bore and into an implantation site.

A further embodiment of the present invention is a subcutaneous implantation instrument for implanting a substantially solid material. An incising body includes a syringe body and an incising shaft. The syringe body and the incising shaft each define a substantially non-circular hollow bore extending continuously along a shared longitudinal axis. The incising shaft includes a beveled tip with a cutting edge on a distal end. Several prismatic or non-cylindrical bore shapes are possible. The incising shaft bore and the syringe body bore both are sized to receive the solid material. A delivery assembly includes a plunger slidably fitted within the syringe body bore. The plunger is conformably shaped to the syringe body bore with an end piece facilitating deployment of the substantially solid material into an implantation site.

A still further embodiment of the present invention is an implantation instrument for implanting a substantially solid material in a subcutaneous location. An incising shaft includes a beveled tip with a cutting edge along a distal end thereof A syringe body is affixed to a proximal end of the incising shaft. The syringe body and the incising shaft each define a substantially non-circular hollow bore extending continuously along a shared longitudinal axis. The incising shaft bore does not exceed the syringe body bore in girth. Both the incising shaft bore and the syringe body bore are sized to receive the solid material. A plunger is conformably shaped to the syringe body bore and has an end piece facilitating deployment of the plunger assembly, the plunger slidably fits within the syringe body bore and advances the solid material through the syringe body bore and the incising shaft bore into the subcutaneous location.

A still further embodiment of the present invention is a method for implanting a substantially solid material in a subcutaneous location. A beveled tip of an incising shaft with a cutting edge along a distal end thereof is inserted into an implantation site. A proximal end of the incising shaft is affixed to a distal end of a syringe body. The syringe body and the incising shaft each define a substantially non-circular hollow bore extending continuously along a shared longitudinal axis. The incising shaft bore do not exceed the syringe body bore in girth. Both the incising shaft bore and the syringe body bore are sized to receive the solid material. The solid material is advanced through the syringe body bore and the incising shaft bore into the subcutaneous location through deployment of a plunger conformably shaped to the syringe body bore. The deployment is effected via actuation of an end piece on a distal end of the plunger. The plunger slidably fits within the syringe body bore.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIGS. 8A–8B are section views illustrating penetration limiting mechanisms for use with the implantation instrument; and FIG. 9 is a perspective view of an instrument for implanting sensors or solid materials in a subcutaneous or other tissue location in accordance with a further embodiment of the present invention.

DETAILED DESCRIPTION

Figure 1:
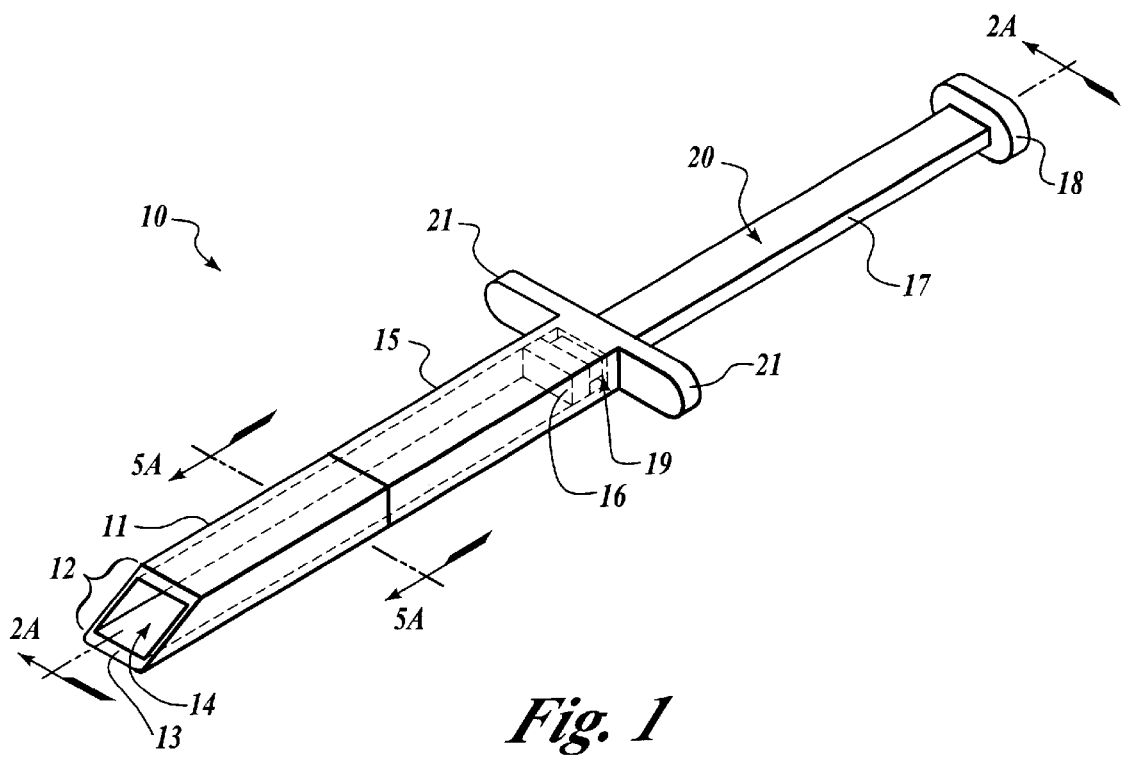
FIG. 1 is a perspective view of an instrument for implanting sensors or solid materials in a subcutaneous or other tissue location in accordance with the present invention.

FIG. 1 is a perspective view of an instrument 10 for implanting sensors or solid materials in a subcutaneous or other tissue location in accordance with the present invention. The implantation instrument 10 consists of two principal groups of components, an incising body consisting of an incising shaft 11 and a syringe body 15, and a delivery assembly consisting of a plunger assembly 20. The delivery assembly is received into the syringe body bore by sliding the plunger assembly 20 through proximal bore opening 19.

The incising shaft 11 is formed with a beveled and rounded tip 12 that tapers into a surgically sharp cutting edge 13 formed on a distal edge. The beveled tip 12 includes a distal bore opening 14 through which the sensor or solid material is delivered into the implantation site.

In the described embodiment, the sensor or solid material (implant) has approximate dimensions of 5 mm by 10 mm by 20 mm. The critical dimension is the cross-sectional profile, that is, the height and width, of the implant which must conform to passage through the syringe body and incising shaft bores. Other nonlinear, prismatic shapes are equally usable provided the implant can fit within the confines of the syringe body and incising shaft bores. The implant could also be folded or compacted to minimize the cross-sectional profile with the implant unfolding or expanding upon implantation. As well, the implant is preferably protected against damage by encasement within, for example, a mannitol pellet in the case of a solid drug delivery system or epoxy in the case of an implantable sensor.

An implantable sensor microchip suitable for use in the present invention is described in PCT Application No. PCT/GB99/02389, to Habib et al., filed Jul. 22, 1998, pending, the disclosure of which is incorporated herein by reference. Such a sensor could be used for monitoring and collecting physiological or chemical measures. Similar devices for therapeutic uses, including treating cancer, and for health care giving, including administering solid medication in the form of boluses, are possible. As well, the present invention has equal applicability to implantation of sensors, including location and identification sensors, and solid materials in domesticated animals. The sensor could also constitute or include a data transmitter with which to exchange information and telemetered signals.

The incising shaft 11 is fixably attached to the syringe body 15 through frictional, adhesive, or preformed constructive means, as is known in the art. Both the incising shaft 11 and syringe body 15 define a substantially non-circular hollow bore extending continuously along a shared longitudinal axis, as further described below with reference to FIGS. 5A–D.

The plunger assembly includes a plunger 16, an interconnecting plunger shaft 17 and a plunger end piece 18. The plunger 16 is conformably shaped to fit within the syringe body bore. The plunger end piece 18 facilitates deployment of the plunger assembly through the syringe body bore and is preferably shaped to fit a thumb or palm impression.

In the described embodiment, the implantation instrument 10 is designed for inexpensive and disposable use utilizing low-cost, sanitizable materials. The incising shaft 11 can be fashioned from surgical grade stainless steel and has the approximate dimensions of approximately 10 mm by 5 mm in cross section. The incising shaft 11 is approximately 50 mm long and the length can be varied to accommodate different implantation depths. The plunger 16 is formed from plastic and rubber and preferably forms a watertight seal within the syringe body bore and has the approximate dimensions of approximately 8 mm by 3 mm in cross section. The plunger shaft 17 and plunger end piece 18 are formed from plastic or similar material. Other materials, as would be recognized by one skilled in the art, could be substituted.

In a further embodiment, the syringe body 15 and plunger assembly can be replaced by an automated injection system, such as used with immunization injection guns or similar devices. These devices typically employ compressed air or other inert gases to administer medication in lieu of manual plungers. Other automated variations include spring-loaded and similar mechanical injection systems. The incising shaft 11 is fixably attached to the automated injection system which functions as a delivery mechanism in place of the syringe body 15 and plunger assembly. Thus, the implant would be pushed through the incising shaft bore using the compressed air or gas, or mechanical equivalent.

Figure 2A:
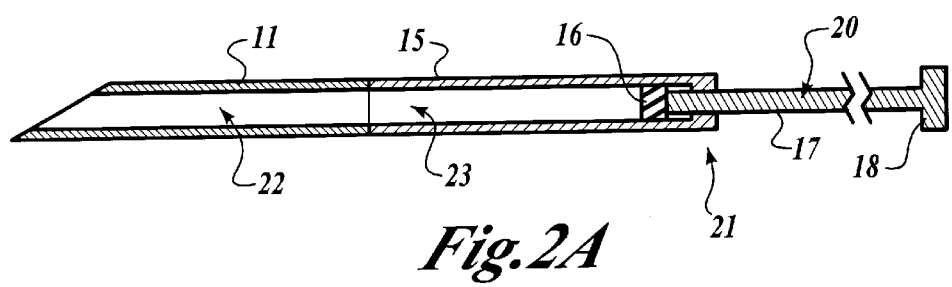
FIG. 2A is a longitudinal cross-sectional view of the implantation instrument with a straight incising shaft.

FIG. 2A is a longitudinal cross-sectional view of the implantation instrument 10 with a straight incising shaft 11. The hollow bore defined by both the incising shaft 11 and the syringe body 15 runs along a common shared axis. The incising shaft bore 22 is sized to allow the implant to advance smoothly into the implantation site under the forward lateral urging of the plunger assembly 20. The syringe body bore 23 must be at least as large as the incising shaft bore 22, but can be slightly larger to accommodate lubricants, anesthetizing agents, or similar coatings, such as mannitol, applied over the sensor or solid material.

The syringe body 15 preferably includes a circular collar 21, pair of winglets, ears, or eyelets, or similar structure, optionally formed on a proximal end of the syringe body 15 to assist a user in depressing the plunger assembly 20.

Figure 2B:
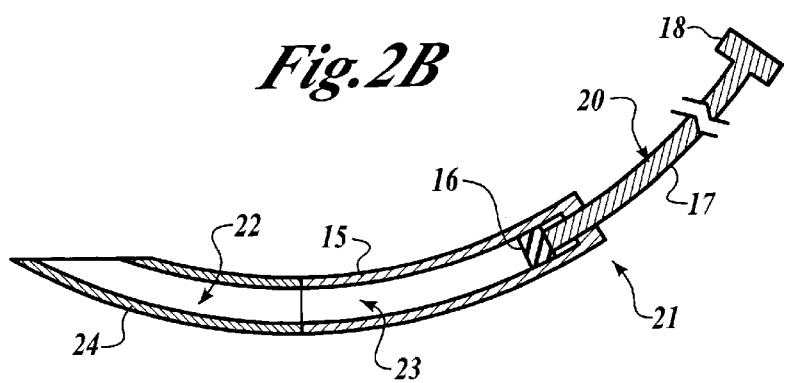
FIG. 2B is a longitudinal cross-sectional view of the implantation instrument with a curved incising shaft.

FIG. 2B is a longitudinal cross-sectional view of the implantation instrument with a curved incising shaft 24. The curved incising shaft 24, as well as the syringe body 15 and related components, are shaped into a substantially continuous curve along the ventral side. The curvature helps regulate the penetration depth of the incising shaft and, in the described embodiment, has an arc of approximately 20 degrees.

Figure 3:
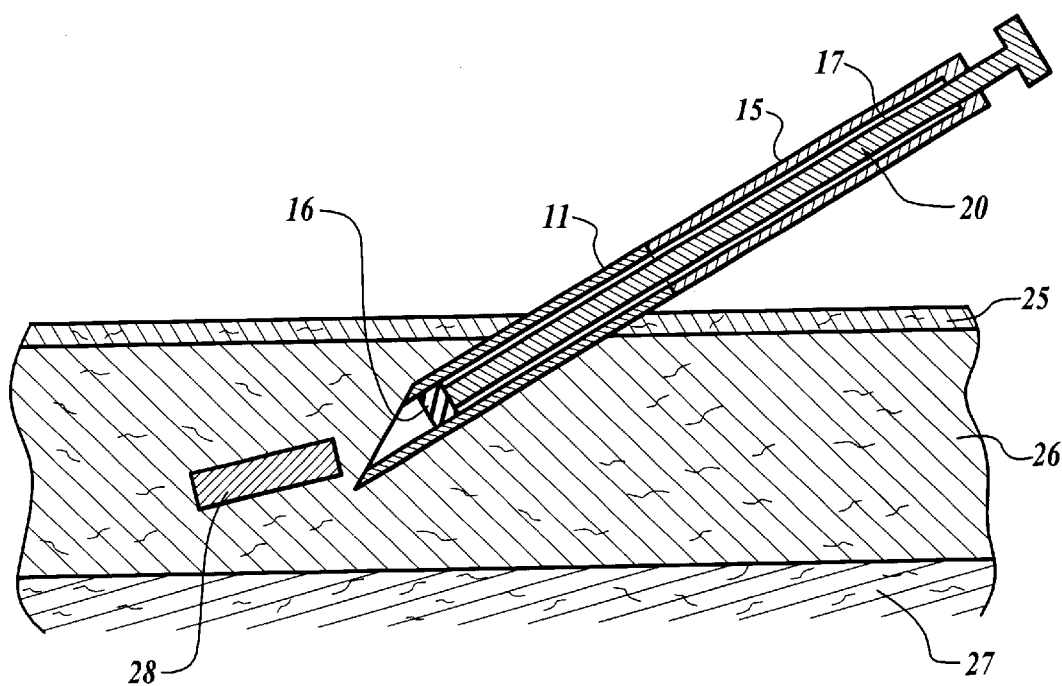
FIG. 3 is a diagrammatic view illustrating the implantation of a sensor or solid material into a subcutaneous site.

FIG. 3 is a diagrammatic view illustrating the implantation of a sensor 28 or solid material into a subcutaneous site. Prior to delivery, the sensor 28 is fed through the proximal bore opening 19 of the syringe body 15 and then further advanced through the syringe body bore 23. During operation, the incising shaft 11 is inserted through the dermis 25 and guided into the layer of subcutaneous fat 26, above the layer of muscle 27. The sensor 28 is then advanced through the incising shaft bore 22 by the plunger 16 into the subcutaneous site. Note that although the foregoing view illustrates an implant into the subcutaneous fat layer, one skilled in the art would appreciate that subcutaneous implantation locations are not strictly limited to the subcutaneous fat layer and are generally termed as those implantation locations situated within a body under the skin.

Figure 4A:
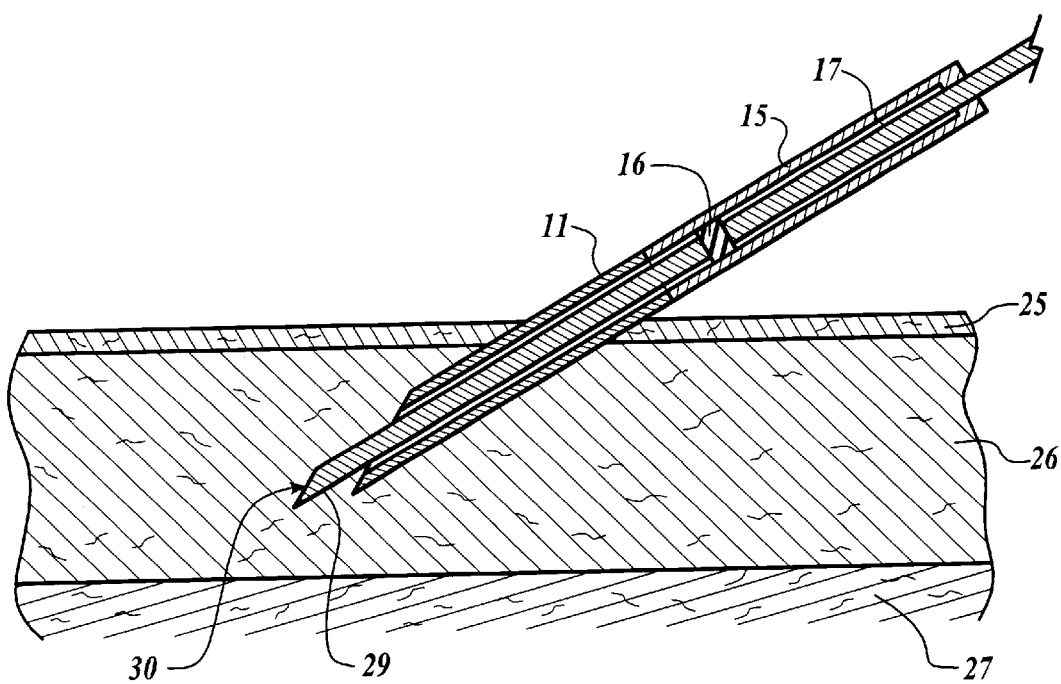
FIG. 4A is a diagrammatic view illustrating the clearing of a subcutaneous site using the implantation instrument fitted with a clearing trocar in accordance with a further embodiment.
Figure 6:
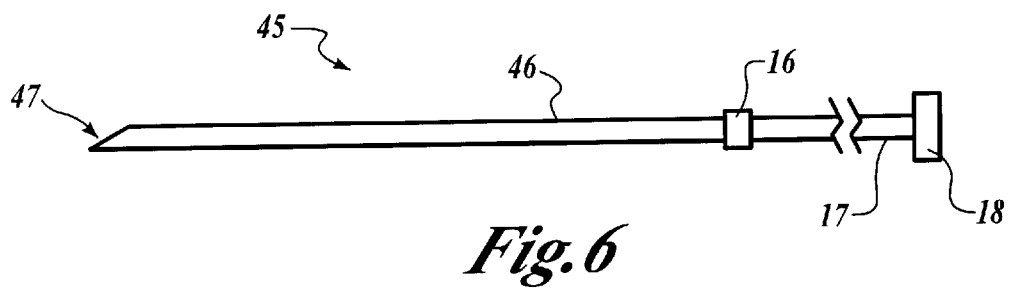
FIG. 6 is a segmented side view of a clearing trocar.

FIG. 4A is a diagrammatic view illustrating the clearing of a subcutaneous site using the implantation instrument 10 fitted with a clearing trocar 29 in accordance with a further embodiment. The clearing trocar 29, as further described below with reference to FIG. 6, is mounted to its own handle or plunger assembly and has a sharp cutting tip 30 for optionally clearing a subcutaneous site prior to delivery of the implant.

Prior to implantation, the clearing trocar 29 is slidably received into the syringe body 15 and is advanced until the cutting tip 30 is even with the proximal bore opening 19 of the incising shaft 11. During operation, the incising shaft 11 and clearing trocar 29 are inserted through the dermis 25 and guided into the layer of subcutaneous fat 26, above the layer of muscle 27.

The cutting edge 13 of the beveled tip 12 makes an entry incision through the dermis 25 and is laterally pushed into the subcutaneous fat 26 until the cutting edge 13 is adjacent to the subcutaneous site. The clearing trocar 29 is then urged through the subcutaneous fat 26 by advancement of its handle or plunger assembly to prepare the implantation site for delivery of the sensor 28 or solid material. The clearing trocar 29 is then withdrawn from the subcutaneous site and out of the implantation instrument 10.

Figure 4B:
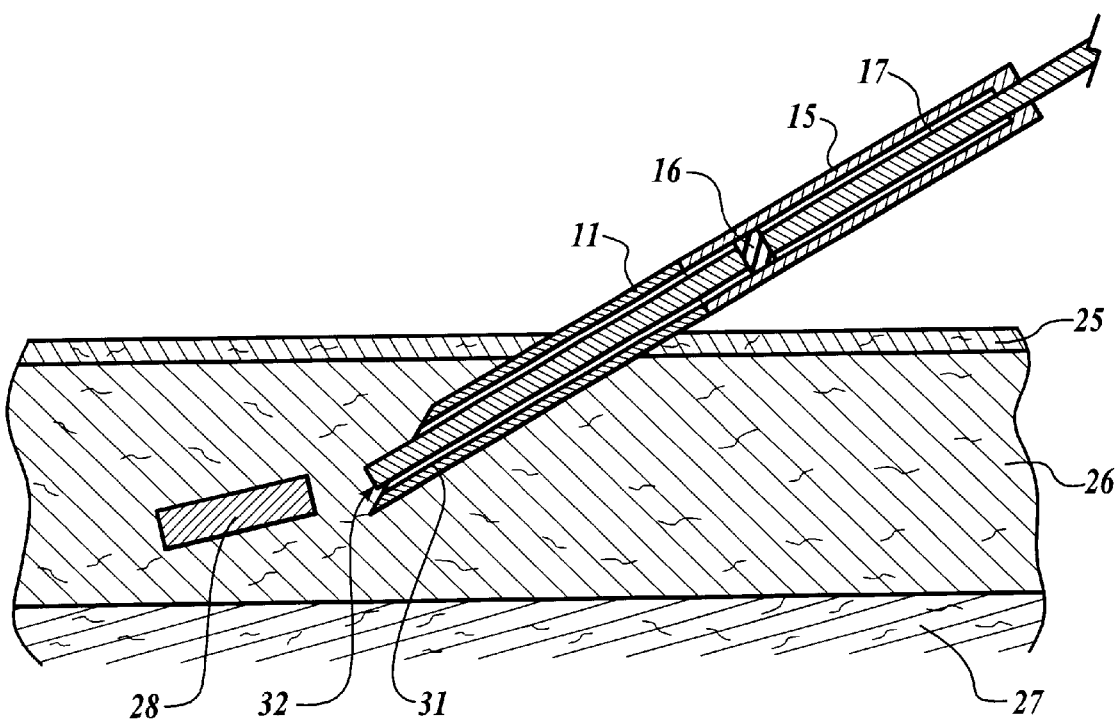
FIG. 4B is a diagrammatic view illustrating the subcutaneous implantation of a sensor using the implantation instrument fitted with a pushing stylet in accordance with a further embodiment.

FIG. 4B is a diagrammatic view illustrating the subcutaneous implantation of a sensor 28 using the implantation instrument 10 fitted with a pushing stylet 31 in accordance with a further embodiment. The pushing stylet 31, as further described below with reference to FIG. 7, has a blunt tip 32 for advancing the sensor 28 (or solid material) through the syringe body bore 23 and incising shaft bore 22 and into the subcutaneous site. The cross section of the pushing stylet 31 closely conforms to the incising shaft bore 22 while the plunger 16 closely conforms to the syringe body bore 23. The pushing stylet 31 thus extends the reach of the plunger assembly 20 and allows the syringe body bore 23 to have a different cross-section than the incising shaft bore 22.

The pushing stylet 31 is used while the incising shaft 11 is in situ in the subcutaneous layer 26. Prior to delivery, the sensor 28 is fed through the proximal bore opening 19 of the syringe body 15 and further advanced within the syringe body bore 23 by contact with the plunger 16. The pushing stylet 31 is slidably received into the syringe body 15 and is advanced until the blunt tip 32 contacts the sensor 28. During operation, the sensor 28 is urged through the incising shaft bore 22 by the pushing stylet 31 and into the subcutaneous site by advancement of the plunger assembly. Upon delivery of the sensor 28 into the subcutaneous site, the incising shaft 11 and pushing stylet 31 are withdrawn.

Although operation of the implantation instrument 10 is described with reference to the implantation of sensors or solid materials into a subcutaneous site situated within the layer of subcutaneous fat 26, implantations could also be effected in other subcutaneous, intramuscular, intraperitoneal, intrathoracic, intracranial, intrajoint, as well as other organ or non-subcutaneous sites, as would be recognized by one skilled in the art. In addition, the foregoing procedure could be modified to forego the use of the clearing trocar 29 for small sensors 28 or solid materials. The clearing effect of the clearing trocar 29 can be approximated by use of the incising shaft 11 alone whereby the incising shaft 11 is inserted into the subcutaneous site and then withdrawn by reverse deployment, thereby forming a slightly overwide implantation site.

The operations of subcutaneous implantation can be carried out over a plurality of sites and with the same or different sensors 28 and solid materials. Similarly, several sensors 28 and solid materials could be implanted at the same subcutaneous site during a single implantation operation.

Figure 5A:
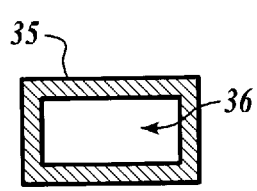
FIGS. 5A–D are transverse cross-sectional views of the implantation instrument illustrating, by way of example, various bore configurations.
Figure 5B:
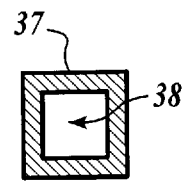
Figure 5C:
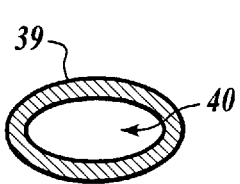
Figure 5D:
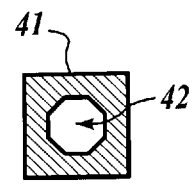

FIGS. 5A–D are transverse cross-sectional views of the implantation instrument 10 illustrating, by way of example, various bore configurations. FIG. 5A illustrates an incising shaft 35 with a substantially rectangular bore 36. FIG. 5B illustrates an incising shaft 37 with a substantially square bore 38. FIG. 5C illustrates an incising shaft 39 with a substantially oval bore 40. And FIG. 5D illustrates an incising shaft 41 with a substantially hexagonal bore 42. Note the circumferential shape of the incising shaft need not follow the internal shape of the incising shaft bore. Other bore configurations, including variations on oval, rectangular, square, pentagonal, hexagonal, heptagonal, octagonal, and similar equilateral or non-equilateral shapes, are feasible.

In the described embodiment, the rectangular bore 36 has the dimensions of approximately 10 mm by 5 mm. The syringe body bore 23 has a length of approximately 5 cm.

FIG. 6 is a segmented side view of a clearing trocar 45. The clearing trocar 45 consists of a beveled tip 47 on the distal end of the clearing trocar 45 and a clearing trocar shaft 46 affixed, either fixably or removably, to the distal end of a plunger 16.

During a clearing operation, the clearing trocar 45 is fully extended from the distal bore opening 14 of the incising shaft 11. The clearing trocar shaft 46 is only long enough to clear out the subcutaneous site. The plunger 16 acts as a stop that limits the extent of penetration of the clearing trocar 45, thereby preventing the clearing trocar 29 from incising too deeply into the subcutaneous fat 29. In addition, the clearing trocar 29 is sized to approximate the girth of the incising shaft bore 22 and will clear a subcutaneous site only as wide as minimally necessary to facilitate implantation of the sensor or solid material. In the described embodiment, the clearing trocar 45 has a length of approximately 2 cm beyond the tip of the syringe body 15.

Figure 7:
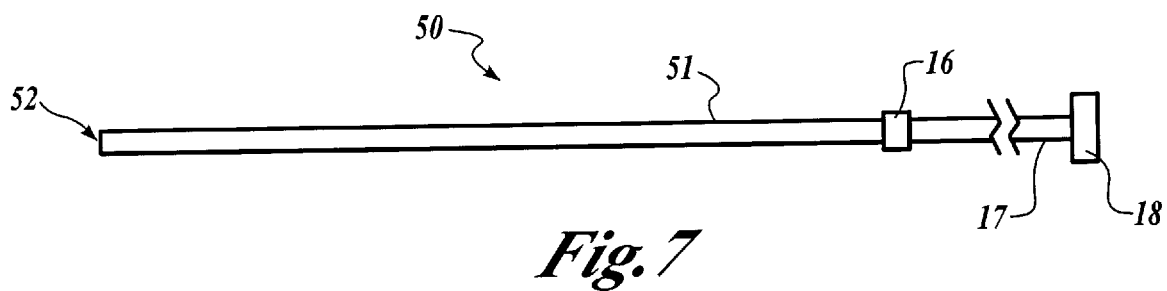
FIG. 7 is a segmented side view of a pushing stylet.

FIG. 7 is a segmented side view of a pushing stylet 50. The pushing stylet 50 consists of a blunt tip 52 on the distal end of the pushing stylet 50 and a pushing stylet shaft 51 affixed, either fixably or removably, to the distal end of a plunger 16.

During a delivery operation, the pushing stylet 50 is extended from the distal bore opening 14 of the incising shaft 11. The pushing stylet shaft 51 is only long enough to clear the distal bore opening 14. The plunger 16 acts as a stop that limits the lateral travel of the pushing stylet 50. In the described embodiment, the pushing stylet 50 has an additional length of approximately 2 cm beyond the tip of the syringe body 15.

FIGS. 8A–8B are section views illustrating penetration limiting mechanisms for use with the implantation instrument 10. The penetration limiting mechanisms limit the depth of penetration of the incising shaft 11 and help prevent excessive penetration. FIG. 8A shows a fixed penetration limiting mechanism consisting of a stopping flange 55 attached to the incising shaft 11. The position of the stopping flange 55 along the incising shaft 11 can be adjusted by loosening a hold-down screw 58 and sliding the stopping flange 55 into the desired location. The lower edge of the stopping flange 55 has a bend 57 with an angle $\tau$, preferably between approximately 30° and 60°, thereby forming an elbow 56 which stops lateral travel upon contact with the skin.

FIG. 8B shows an adjustable penetration limiting mechanism consisting of a stopping flange 60 attached a frictional collar 64. The stopping flange 60 and frictional collar 64 are slidably attached to the incising shaft 11. An adjustable collar 64, preferably in threaded communication 65 with the frictional collar 64, manually stops deployment of the penetration limiting mechanism by tightening the frictional collar 64 against the incising shaft 11. The lower edge of the stopping flange 60 has a bend 62 with an angle $\upsilon$, preferably between approximately 30° and 60°, thereby forming an elbow 61 which stops lateral travel upon contact with the skin.

FIG. 9 is a perspective view of an instrument for implanting sensors or solid materials in a subcutaneous or other tissue location in accordance with a further embodiment of the present invention. The instrument is equipped with the stopping flange 55 shown in FIG. 8A. Other forms of penetration limiting mechanisms, both fixed and adjustable, could be used, as would be readily apparent to one skilled in the art.

While the invention has been particularly shown and described as referenced to the embodiments thereof, those skilled in the art will understand that the foregoing and other changes in form and detail may be made therein without departing from the spirit and scope of the invention.

What is claimed is:

1. A subcutaneous implantation instrument for implanting a substantially solid material, comprising:
    an incising body comprising a syringe body and an incising shaft which each define a substantially non-circular hollow bore extending continuously along a shared longitudinal axis, the incising shaft comprising a beveled tip with a cutting edge on a distal end, the incising shaft bore and the syringe body bore both being sized to receive the solid material;
    a delivery assembly comprising a plunger slidably fitted within the syringe body bore, the plunger conformably shaped to the syringe body bore with an end piece facilitating deployment of the substantially solid material into an implantation site; and
    a clearing assembly comprising a plunger and a clearing trocar slidably fitted within the syringe body bore, the plunger conformably shaped to the syringe body bore with an end piece facilitating deployment, the clearing trocar closely fitting within the incising shaft bore and affixed to a distal end of the plunger.

2. A subcutaneous implantation instrument for implanting a substantially solid material, comprising:
    an incising body comprising a syringe body and an incising shalt which each define a substantially non-circular hollow bore extending continuously along a shared longitudinal axis, the incising shaft comprising a beveled tip with a cutting edge on a distal end, the incising shaft bore and the syringe body bore both being sized to receive the solid material; and
    a delivery assembly comprising a plunger slidably fitted within the syringe body bore, the plunger conformably shaped to the syringe body bore with an end piece facilitating deployment of the substantially solid material into an implantation site and a pushing stylet slidably fitting within the incising shaft bore and affixed to a distal end of the plunger.

3. A subcutaneous implantation instrument for implanting a substantially solid material, comprising:
    an incising body comprising a syringe body and an incising shaft which each define a substantially non-circular hollow bore extending continuously along a shared longitudinal axis, the incising shaft comprising a beveled tip with a cutting edge on a distal end, the incising shaft bore and the syringe body bore both being sized to receive the solid material, the incising body further comprising a stopping flange mounted circumferentially on the syringe body; and
    a delivery assembly comprising a plunger slidably fitted within the syringe body bore, the plunger conformably shaped to the syringe body bore with an end piece facilitating deployment of the substantially solid material into an implantation site.

4. A subcutaneous implantation instrument in accordance with claim 3, wherein the stopping flange is slidably mounted on the syringe body.

5. An implantation instrument for implanting a substantially solid material in a subcutaneous location, comprising:
    an incising shaft comprising a beveled tip with a cutting edge along a distal end thereof;
    a syringe body affixed to a proximal end of the incising shaft, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;
    a plunger conformably shaped to the syringe body bore and having an end piece facilitating deployment of the plunger assembly, the plunger slidably fitting within the syringe body bore and advancing the solid material through the syringe body bore and the incising shaft bore into the subcutaneous location; and
    a clearing trocar conformably shaped to the incising shaft bore and affixed to and substantially centered on the distal end of the plunger, the clearing trocar and a pushing stylet slidably fitting within the non-circular bore of the syringe body.

6. An implantation instrument for implanting a substantially solid material in a subcutaneous location, comprising:
    an incising shaft comprising a beveled tip with a cutting edge along a distal end thereof;
    a syringe body affixed to a proximal end of the incising shaft, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;
    a plunger conformably shaped to the syringe body bore and having an end piece facilitating deployment of the plunger assembly, the plunger slidably fitting within the syringe body bore and advancing the solid material through the syringe body bore and the incising shaft bore into the subcutaneous location; and
    a pushing stylet smaller than the incising shaft bore and affixed to the distal end of the plunger assembly, the pushing stylet slidably fitting within the syringe body bore.

7. An implantation instrument for implanting a substantially solid material in a subcutaneous location, comprising:
    an incising shaft comprising a beveled tip with a cutting edge along a distal end thereof;
    a syringe body affixed to a proximal end of the incising shaft, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;
    a plunger conformably shaped to the syringe body bore and having an end piece facilitating deployment of the plunger assembly, the plunger slidably fitting within the syringe body bore and advancing the solid material through the syringe body bore and the incising shaft bore into the subcutaneous location; and a penetration limiting mechanism comprising a stopping flange mounted circumferentially along an exterior surface of the syringe body and limiting subcutaneous penetration by the instrument.

8. An implantation instrument for implanting a substantially solid material in a subcutaneous location, comprising:

an incising shaft comprising a beveled tip with a cutting edge along a distal end thereof;

a syringe body affixed to a proximal end of the incising shaft, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;

a plunger conformably shaped to the syringe body bore and having an end piece facilitating deployment of the plunger assembly, the plunger slidably fitting within the syringe body bore and advancing the solid material through the syringe body bore and the incising shaft bore into the subcutaneous location; and an adjustable penetration limiting mechanism comprising:
  a stopping flange limiting subcutaneous penetration by the instrument;
  a frictional collar affixed to the stopping flange and slidably and circumferentially mounted along an exterior surface of the syringe body; and
  an adjustable collar stay limiting movement of the frictional collar.

9. A method for implanting a substantially solid material in a subcutaneous location, comprising:

inserting a beveled tip of an incising shaft with a cutting edge along a distal end thereof into an implantation site, a proximal end of the incising shaft being affixed to a distal end of a syringe body, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;

advancing the solid material through the syringe body bore and the incising shaft bore into the subcutaneous location through deployment of a plunger conformably shaped to the syringe body bore, the deployment being effected via actuation of an end piece on a distal end of the plunger, the plunger slidably fitting within the syringe body bore; and preparing the implantation site using a clearing trocar conformably shaped to the incising shaft bore and affixed to and substantially centered on the distal end of the plunger, the clearing trocar and the pushing stylet slidably fitting within the non-circular bore of the syringe body.

10. A method for implanting a substantially solid material in a subcutaneous location, comprising:

inserting a beveled tip of an incising shaft with a cutting edge along a distal end thereof into an implantation site, a proximal end of the incising shaft being affixed to a distal end of a syringe body, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;

advancing the solid material through the syringe body bore and the incising shaft bore into the subcutaneous location through deployment of a plunger conformably shaped to the syringe body bore, the deployment being effected via actuation of an end piece on a distal end of the plunger, the plunger slidably fitting within the syringe body bore; and delivering the solid material into the implantation site through a pushing stylet smaller than the incising shaft bore and affixed to the distal end of the plunger assembly, the pushing stylet slidably fitting within the syringe body bore.

11. A method for implanting a substantially solid material in a subcutaneous location, comprising:

inserting a beveled tip of an incising shaft with a cutting edge along a distal end thereof into an implantation site, a proximal end of the incising shaft being affixed to a distal end of a syringe body, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;

advancing the solid material through the syringe body bore and the incising shaft bore into the subcutaneous location through deployment of a plunger conformably shaped to the syringe body bore, the deployment being effected via actuation of an end piece on a distal end of the plunger, the plunger slidably fitting within the syringe body bore; and limiting the insertion of the instrument through a penetration limiting mechanism comprising a stopping flange mounted circumferentially along an exterior surface of the syringe body and limiting subcutaneous penetration by the instrument.

12. A method for implanting a substantially solid material in a subcutaneous location, comprising:

inserting a beveled tip of an incising shaft with a cutting edge along a distal end thereof into an implantation site, a proximal end of the incising shaft being affixed to a distal end of a syringe body, the syringe body and the incising shaft each defining a substantially non-circular hollow bore extending continuously along a shared longitudinal axis, the incising shaft bore not exceeding the syringe body bore in girth, both the incising shaft bore and the syringe body bore being sized to receive the solid material;

advancing the solid material through the syringe body bore and the incising shaft bore into the subcutaneous location through deployment of a plunger conformably shaped to the syringe body bore, the deployment being effected via actuation of an end piece on a distal end of the plunger, the plunger slidably fitting within the syringe body bore; and limiting the insertion of the instrument through an adjustable penetration limiting mechanism comprising a stopping flange limiting subcutaneous penetration by the instrument, a frictional collar affixed to the stopping flange and slidably and circumferentially mounted along an exterior surface of the syringe body, and an adjustable collar stay limiting movement of the frictional collar.

* * * * *

UNITED STATES PATENT AND TRADEMARK OFFICE
CERTIFICATE OF CORRECTION

PATENT NO. : 6,436,068 B1
DATED : August 20, 2002
INVENTOR(S) : Bardy

It is certified that error appears in the above-identified patent and that said Letters Patent is hereby corrected as shown below:

Column 9,
Line 39, "incising shalt which each define a substantially non-" should read -- incising shaft which each define a substantially non --

Signed and Sealed this

Fourteenth Day of January, 2003

JAMES E. ROGAN
*Director of the United States Patent and Trademark Office*